(12) United States Patent
Black et al.

(10) Patent No.: US 8,511,823 B2
(45) Date of Patent: Aug. 20, 2013

(54) IMAGING SYSTEM

(75) Inventors: Stephen H. Black, Buellton, CA (US);
Andrew D. Portnoy, Denver, CO (US);
Alan G. Silver, Allen, TX (US)

(73) Assignee: Raytheon Company, Waltham, MA (US)

( * ) Notice: Subject to any disclaimer, the term of this patent is extended or adjusted under 35 U.S.C. 154(b) by 164 days.

(21) Appl. No.: 13/026,854

(22) Filed: Feb. 14, 2011

(65) Prior Publication Data

US 2011/0199578 A1 Aug. 18, 2011

Related U.S. Application Data

(60) Provisional application No. 61/305,826, filed on Feb. 18, 2010.

(51) Int. Cl.
*A61B 3/14* (2006.01)
*A61B 3/00* (2006.01)

(52) U.S. Cl.
USPC .......................................... 351/206; 351/246

(58) Field of Classification Search
USPC .......................................... 351/206, 205, 246
See application file for complete search history.

(56) References Cited

U.S. PATENT DOCUMENTS

2002/0105584 A1 8/2002 Jung et al.
2004/0095492 A1 5/2004 Baxter et al.
2007/0029484 A1 2/2007 Anderson et al.

FOREIGN PATENT DOCUMENTS

EP 1 089 555 A1 4/2001

OTHER PUBLICATIONS

Communication from European Patent Office dated May 12, 2011, European Search Report for Application No. 11154913.5 2202, 7 pages.
Shankar, Mohan, "*Sampling and Signal Estimation in Computational Optical Sensors*", Dissertation submitted in partial fulfillment of the requirements for the degree of Doctor of Philosophy in the Department of Electrical and Computer Engineering in the Graduate School of Duke University, 140 pages, 2007.
Pending U.S. Appl. No. 12/855,472, filed Aug. 12, 2010 by Andrew D. Portnoy, entitled "*System, Method, and Software for Image Processing*", 29 total pages.

*Primary Examiner* — Jack Dinh
(74) *Attorney, Agent, or Firm* — Lando & Anastasi, LLP

(57) ABSTRACT

According to certain embodiments, foveal array elements of a foveal region of a focal plane array are sampled at a faster sampling rate to yield foveal array data. Peripheral array elements of a peripheral region of the focal plane array are sampled at a slower sampling rate or sparser sampling density to yield peripheral array data. The foveal array data is processed to yield foveal image data for a foveal region of a display. The peripheral array data is processed to yield peripheral image data for a peripheral region of the display.

18 Claims, 4 Drawing Sheets

IMAGING SYSTEM

RELATED APPLICATION

This application claims benefit under 35 U.S.C. §119(e) of U.S. Provisional Application Ser. No. 61/305,826, entitled "Imaging System," filed Feb. 18, 2010, by Stephen H. Black et al., which is incorporated herein by reference.

BACKGROUND

An imaging system may have a detector that generates a signal in response to detecting light from a scene, a processor that processes the signal, and a display that displays an image of the scene using the processed signal. In certain situations, signal processing may increase the size, weight, computational, and/or power burden. Accordingly, in certain situations, processing may be reduced to decrease these burdens.

SUMMARY OF THE DISCLOSURE

In accordance with the present invention, disadvantages and problems associated with previous techniques for imaging systems may be reduced or eliminated.

According to certain embodiments, foveal array elements of a foveal region of a focal plane array are sampled at a faster sampling rate to yield foveal array data. Peripheral array elements of a peripheral region of the focal plane array are sampled at a slower sampling rate or sparser sampling density to yield peripheral array data. The foveal array data is processed to yield foveal image data for a foveal region of a display. The peripheral array data is processed to yield peripheral image data for a peripheral region of the display.

Certain embodiments of the invention may provide one or more technical advantages. A technical advantage of one embodiment may be that processing data for a peripheral region may be reduced relative to processing data for a foveal region, which may reduce burdens on the imaging system. Another technical advantage of one embodiment may be that the foveal region can be adjusted.

Certain embodiments of the invention may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION OF THE DRAWINGS

Figure 1:
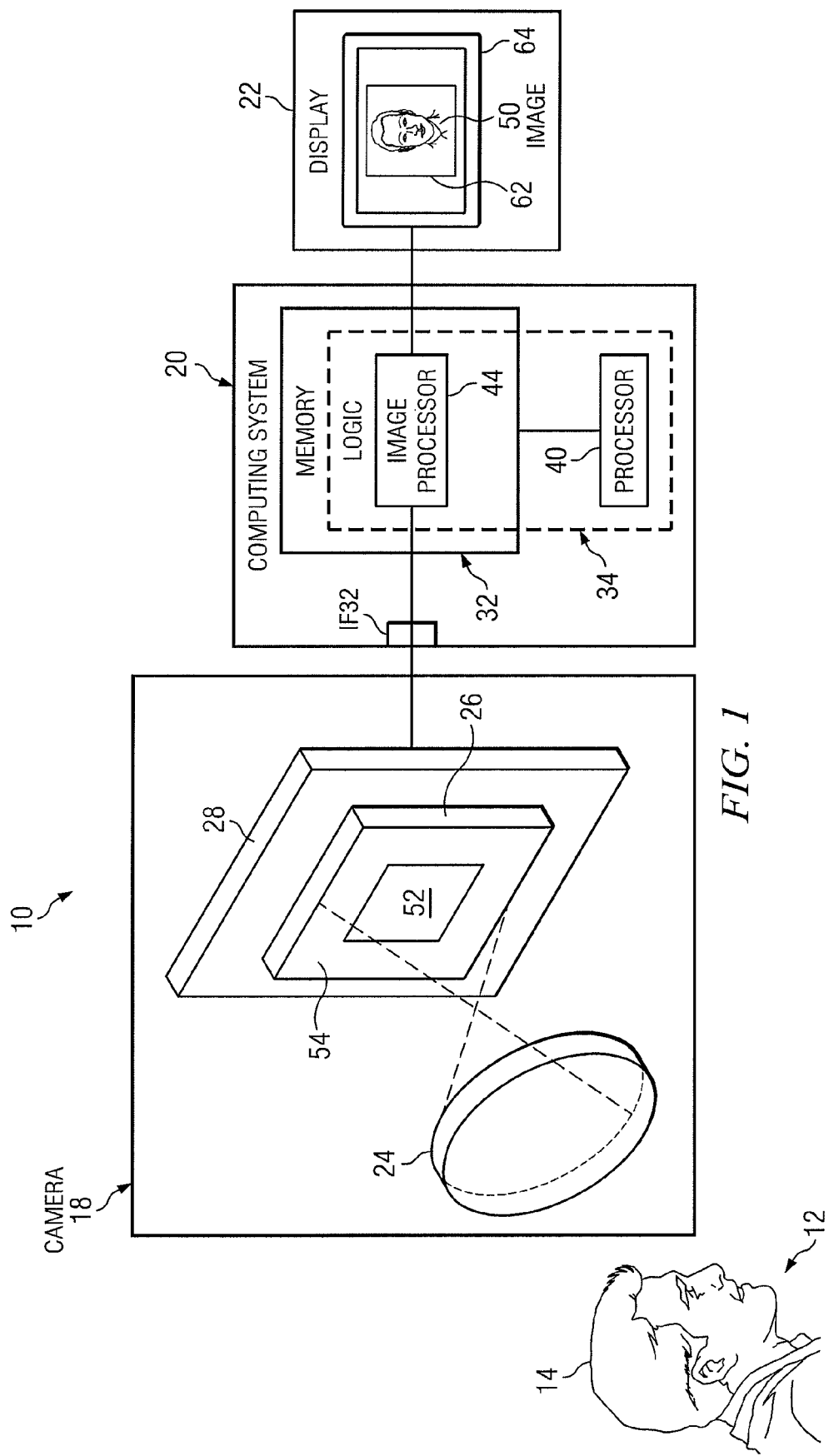
FIG. 1 illustrates an example of an imaging system that may be used to generate an image of a scene.
Figure 2A:
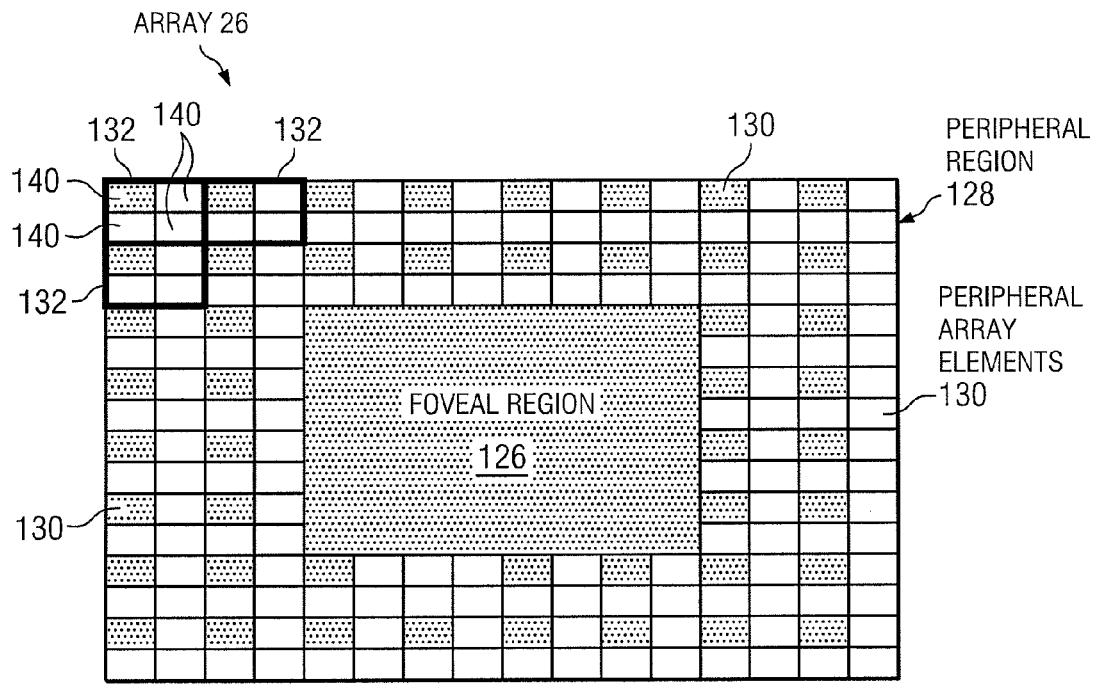
FIGS. 2A through 2D illustrate an example of a method for sampling a focal plane array.
Figure 2B:
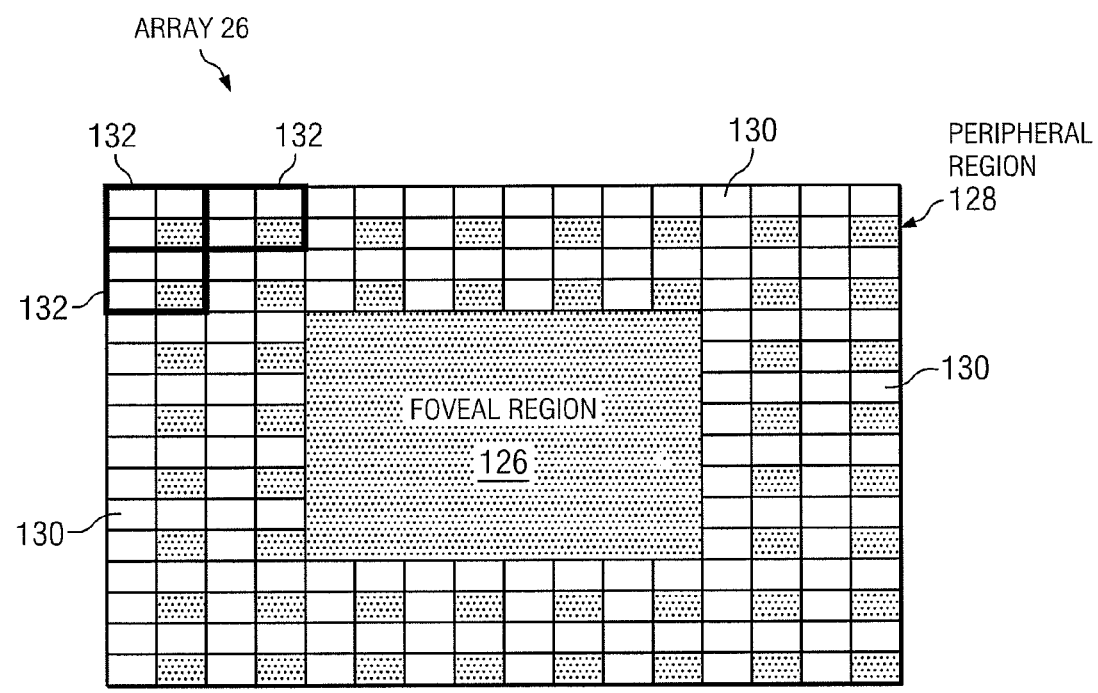
Figure 2C:
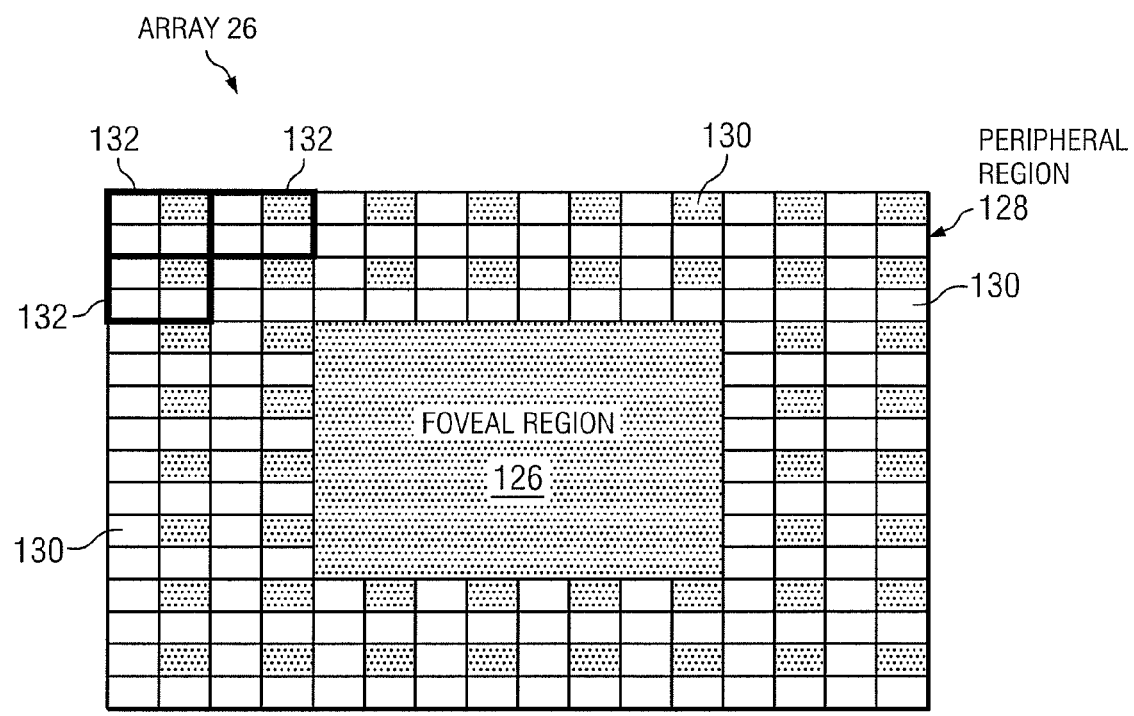
Figure 2D:
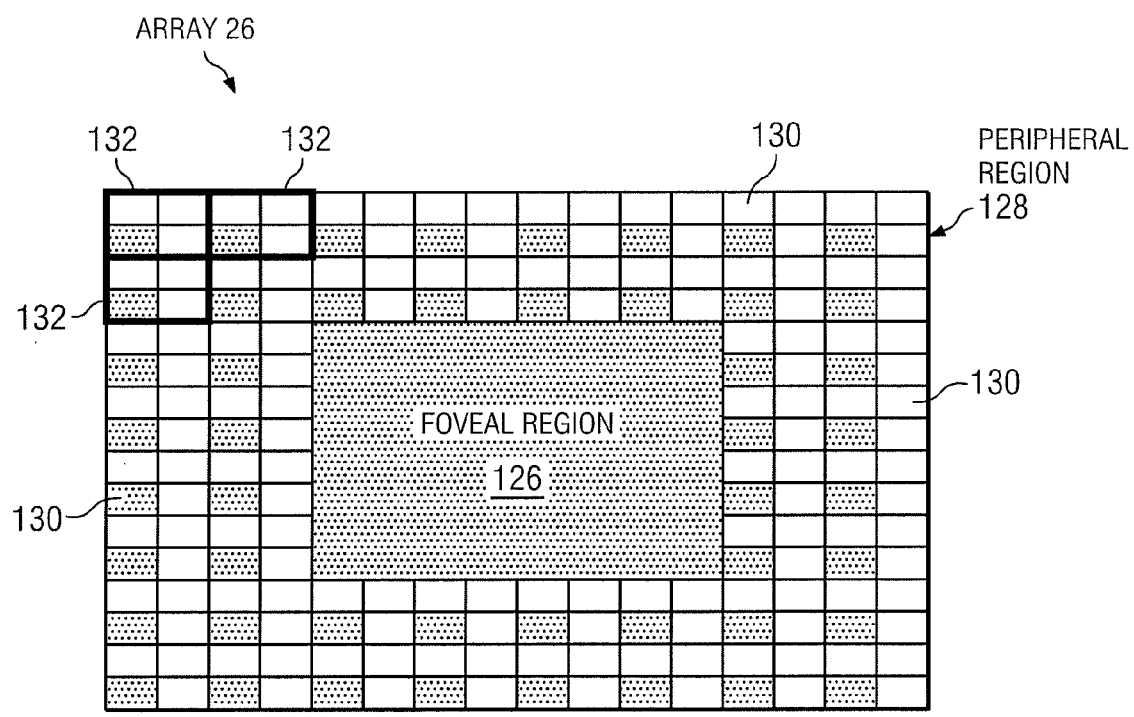
Figure 3:
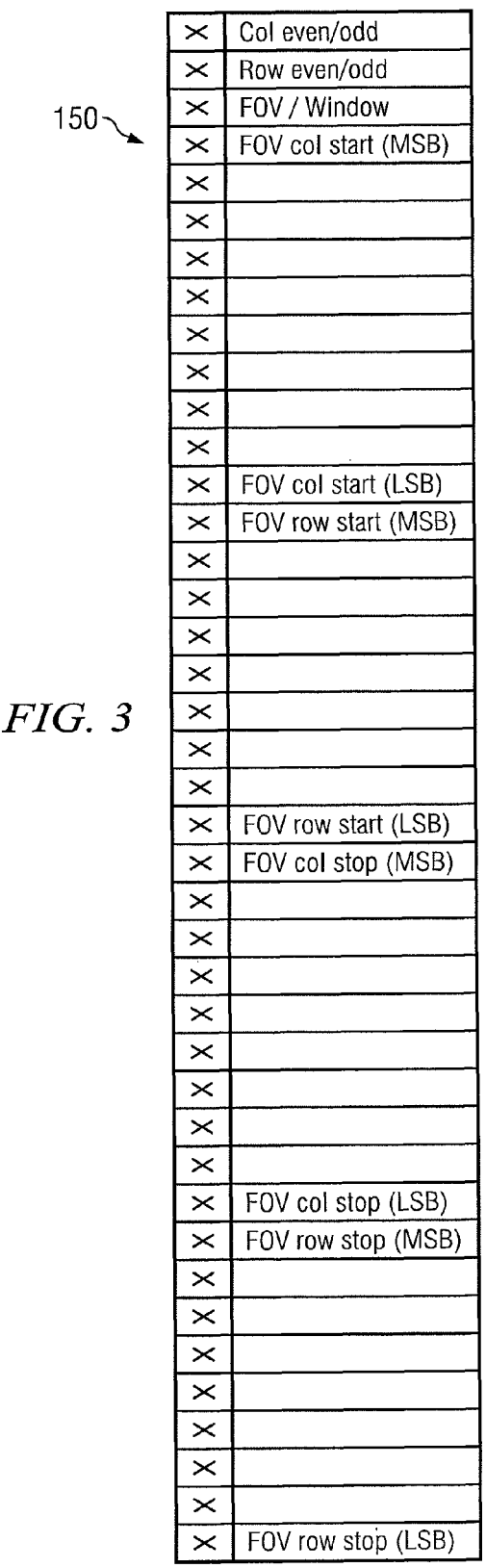
FIG. 3 illustrates an example of a messaging sequence that may be used to set the size of a foveal region of a focal plane array.

Embodiments of the present invention and its advantages are best understood by referring to FIGS. 1 through 3 of the drawings, like numerals being used for like and corresponding parts of the various drawings.

FIG. 1 illustrates an example of an imaging system 10 that may be used to generate an image 50 of a scene 12. In the illustrated example, scene 12 includes objects 14. System 10 includes a camera 18, a computing system 20, and a display 22 coupled as shown. Camera 18 includes optics 24, a focal plane array (or detector array) 26, and integrated circuit 28. Focal plane array 26 includes a focal region 52 and a peripheral region 54. Computing system 20 includes an interface 32, logic 34, and a memory 36. Logic 34 includes one or more processors 40 and applications such as an image processor 44. Memory 36 stores applications. Display 22 displays image 50 of scene 12. Display 22 has a foveal region 62 and a peripheral region 64.

In certain examples of operation, system 10 may sample foveal array elements of foveal region 52 of focal plane array 26 at a faster sampling rate to yield foveal array data. System 10 may sample peripheral array elements of peripheral region 54 of focal plane array at a slower sampling rate to yield peripheral array data. System 10 may process the foveal array data to yield foveal image data for foveal region 62 of display 22, and may process the peripheral array data to yield peripheral image data for peripheral region 64 of display 22.

In the illustrated example, scene 12 includes objects 14 that reflect and/or emit light that may be used to generate image 50 of scene 12. Camera 18 receives light from scene 12. Optics 24 refracts or reflects the light to direct the light towards focal plane array 26. Optics 24 may comprise one or more optical devices such as lenses. Focal plane array 26 may comprise an array (such as a two-dimensional array) of detector elements that can detect light and generate detector signals in response to the detected light. The detector signal corresponding to a detector element includes array data that represents the amount and/or wavelength of light that is detected by the detector element. Examples of focal plane arrays include complementary metal-oxide-semiconductor (CMOS) imagers, charge coupled devices, hybrid infrared imagers, and uncooled microbolometers.

In certain embodiments, focal plane array 26 may have foveal region 52 that comprises foveal array elements and peripheral region 54 that comprises peripheral array elements. Focal plane array 26 may generate array data (which may also be referred to as focal plane array, focal plane, or detector data). The focal plane array's foveal region 52 may generate foveal data (such as foveal array data), which may be used to generate foveal region 62 of display 22 (display foveal region). The focal plane array's peripheral region 54 may generate peripheral data (such as peripheral array data), which may be used to generate peripheral region 64 of display 22 (or display peripheral region).

Foveal regions 52 and 62 may have any suitable size and shape, and may comprise any portion of array 26 and display 22, respectively. In certain embodiments, a foveal region 52 and/or 62 corresponds to the foveal portion of an eye's field-of-view, which detects visual information with greater precision than the peripheral region of the field-of-view. In the embodiments, foveal regions 52 and 62 may be located near or at the central portion of array 26 and display 22, respectively, and the peripheral regions 54 and 64 may surround the foveal regions 52 and 62, respectively.

In certain embodiments, the size and position of foveal regions 52 and 62 and/or peripheral regions 54 and 64 may be changed. For example, a foveal region 52 or 62 may be moved from the center to the upper left corner. As another example, foveal region 52 or 62 may be made smaller or larger. In certain embodiments, the size and position of a foveal region 52 or 62 may be determined according to image 50. For example, image 50 may include an element of interest that moves, and foveal region 52 or 62 may move where the element moves. An example of a method for changing the foveal region is described in more detail with reference to FIG. 3.

Integrated circuit 28 controls operation of and/or processes signals from focal plane array 26. In certain embodiments, integrated circuit 28 reads and outputs the detector signals. An example of integrated circuit 28 is a read-out integrated circuit (RoIC) 28. Integrated circuit 28 may output the signals according to any suitable protocol, such as the National Television System Committee (NTSC) protocol, Phase Alternating Line (PAL) protocol, or sequential color with memory (SECAM) protocol.

Integrated circuit 28 may include several components that control operation of and/or processes signals from focal plane array 26. In certain embodiments, integrated circuit 28 includes power circuitry that controls power to array 26, timing circuitry that provides clock signals, synchronization circuitry that synchronizes the timing of array 26, amplifying circuitry that amplifies signals from array 26, filter circuitry that filters signals from array 26, and/or an analog-to-digital (A/D) circuitry that digitizes video signals generated by array 26.

Computing system 20 facilitates the operation of and/or processes signals of system 10. In certain embodiments, image processor 44 processes array data from camera 12 to yield image data used to display image 50 on display 22. Image data for a pixel of image 50 may indicate the amount and/or wavelength of light detected by a detector element that corresponds to the pixel. A scan of substantially all of focal plane array 26 may yield a frame of data. A frame of focal plane data may be used to generate a frame of image data used to display image 50 at a particular time. Frames may be generated at successive times to yield a moving image 50 of scene 12.

In certain embodiments, image processor 44 may perform other suitable operations. For example, image processor 44 may perform a sharpening operation on focal plane data to sharpen image 50. As another example, image processor 44 may perform an image recognition operation that detects certain features, such as colors or outlines.

Display 50 may be any suitable device configured to display image 50 of scene 12 using image data. In certain embodiments, display 50 comprises display foveal region 62 and display peripheral region 64. Display foveal region 62 generates a portion of image 50 from foveal image data, which is in turn generated from foveal focal plane data from focal plane's foveal region 52. Display peripheral region 64 generates a portion of image 50 from peripheral image data, which is in turn generated from peripheral array data from detector peripheral region 54.

Display 22 may be any suitable size and/or shape. The reduced processing may allow for applications in devices with size and/or weight restrictions and/or limited computational and/or power resources. In certain embodiments, display 50 is sufficiently small to be placed in close proximity (such as less than 1, 1 to 2, or 2 to 5 inches) to a human eye such that image 50 fits within the vision of the eye. Examples of such displays 50 include head mounted displays (HMDs) and displays for eyepieces of optical devices, such as binoculars or telescopes. Head mounted displays are devices that may be worn by a user and include a relatively small computer display that is positioned in front of the user's eyes.

In certain embodiments of operation, focal plane array 26 may selectively scan certain detector elements and not scan other regions. In certain embodiments, a controller (such as drive circuit 28 and/or image processor 44) may instruct focal plane array 26 to scan the detector elements. In certain embodiments, a smaller percentage of focal plane array peripheral region 54 may be sampled in a unit of time, and a larger percentage of focal plane array foveal region 52 may be sampled in the unit of time. In the embodiments, the data processing of system 10 may be less than that of a system that samples the higher percentage for both focal plane array peripheral region 54 and focal plane array foveal region 52.

In certain embodiments, foveal array elements may be sampled at a faster sampling rate to yield foveal array data, and peripheral array elements may be sampled at a slower sampling rate to yield peripheral focal plane array data. The sampling rate may represent the number of elements sampled per unit time. Examples of a faster sampling rate include a rate in the ranges of 10 to 20, to 30, and 30 or more frames per second. A slower sampling rate may be a sampling rate that is less than the faster sampling rate, that is, $R_S < R_F$, where $R_S$ represents the slower sampling rate and $R_F$ represents the faster sampling rate. Examples of a slower sampling rate include $R_S = 1/n\, R_F$, where n is a positive integer, such as an integer in the ranges of 2 to 4, 4 to 8, or greater than 8.

FIGS. 2A through 2D illustrate an example of a method for sampling focal plane array 26 that may be used with system 10 of FIG. 1. Array 26 includes foveal region 126 comprising foveal array elements and peripheral region 128 comprising peripheral array elements 130. In the illustrated example, peripheral array elements 130 are organized into sub-regions 132. Each sub-region 132 may comprise two or more peripheral array elements 130, and may comprise any suitable shape. For example, sub-region 132 may comprise m×n peripheral array elements 130, and may be a m×n rectangle, where m represents the number of rows and n represents the number of columns of elements 130.

Each sub-region 132 may comprise two or more subsets 140. Each subset 140 may include one or more peripheral array elements 130 that are sampled for a frame. In certain examples, a first subset 140 is sampled for a first frame, and a second subset 140 is sampled for a second frame. In the illustrated example, a sub-region 132 has four peripheral array elements 130 arranged in a 2×2 rectangle. Sub-region 132 has four subsets 140, where each subset 140 includes one peripheral array element 130

Foveal region 126 may be scanned at a faster scanning rate, while peripheral region 128 may be scanned at a slower scanning rate. In certain embodiments, a proper subset of each sub-region 132 of peripheral region 128 may be scanned for a frame. A proper subset of set S is a subset that is strictly contained in S and so excludes at least one member of S. That is, not all elements of sub-region 132 are scanned at each frame.

In certain embodiments, different elements of a sub-region 132 may be scanned for different frames. For example, a first subset of the sub-region 132 may be sampled for a first frame, and a second subset of the sub-region 132 may be sampled for a second frame, where the second subset not equal to the first subset. Two sets are not equal if they do not have the same elements. Unequal sets may have at least one common element or may have no common elements.

FIGS. 2A through 2D illustrate scanning for four frames. Substantially all of foveal region 126 is scanned for each frame. Different subsets 140 of peripheral region 128 are scanned for different frames. For example, subset 140 of the upper left corner of each sub-region 132 may be scanned for a first frame as shown in FIG. 2A. Subset 140 of the lower right corner of each sub-region 132 may be scanned for a second frame as shown in FIG. 2B. Subset 140 of the upper right corner of each sub-region 132 may be scanned for a third frame as shown in FIG. 2C. Subset 140 of the lower left corner of each sub-region 132 may be scanned for a fourth frame as shown in FIG. 2D. In the example, sub-regions 132 are processed with a 75 percent reduction in processing load.

The scanning may be adjusted in any suitable manner. For example, if power is running low, the sampling rate may be decreased, or if power is increased, the sampling rate may be increased. As another example, a user may request a faster or slower scanning rate. As another example, system 10 may detect increased motion of scene and may increase the sampling rate, or may detect decreased motion of scene 12 and may decrease the sampling rate.

Image processor 44 may process the array data in any suitable manner to generate image 50. In certain embodiments, image processor 44 may process peripheral array data from a first subset 140 to yield first image data for a first frame. The first subset 140 is not sampled for the next frame, so the first image data is utilized for the next frame. The first image data may be utilized in any suitable manner. For example, the first image data may be held for the next frame. As another example, the first image data may be averaged with second image data generated using a second subset 140, and the averaged data may be used for the next frame. In certain embodiments, image processor 44 may use first image data generated using a first subset 140 for a first frame and a second frame, and may use second image data using a second subset 140 for a second frame and a third frame.

FIG. 3 illustrates an example of a messaging sequence 150 that may be used to set the size of a foveal region of a focal plane array 26. Messaging sequence 150 may be used to communicate among the components of system 10, such as among camera 18, computing system 20, and/or display 22. For example, messaging sequence 150 may be used to communicate array data from camera 12 to display 22, camera settings or scanning instructions from computing system 20 to camera 18, or instructions for displaying image to image processor 44 or display 22.

In the illustrated example, messaging sequence 150 may be used to instruct integrated circuit 28 to set or change the size of the detector foveal region. Messaging sequence 150 indicates the array elements that are designated as foveal array elements. In the example, messaging sequence 150 includes fovea start addresses and fovea stop addresses. A fovea start address may be a row start address that indicates the start of a row of the foveal region, or may be a column start address that indicates the start of a column of the foveal region, or a combination of both the row and column starting address. A fovea stop address may be a row stop address that indicates the end of a row of the foveal region, or may be a column stop address that indicates the end of a column of the foveal region, or a combination of both the row and column ending address. In other examples, messaging sequence 150 may be used to instruct integrated circuit 28 to set or change the size of the detector peripheral region.

In particular embodiments, a focal plane may be an array of microbolometers. In these embodiments, provisions may be made to accommodate changes in microbolometer Joule heating as the sampling rate is varied relative to the foveal region. For example, a constant bias duty cycle may be maintained on the microbolometer as the sampling rate is changed. As another example, changes in the bolometer's resistance due to Joule heating may be compensated for by electronically adjusting the microbolometer's bias conditions or the operating bias in supporting circuitry.

Modifications, additions, or omissions may be made to the systems and apparatuses disclosed herein without departing from the scope of the invention. The components of the systems and apparatuses may be integrated or separated. Moreover, the operations of the systems and apparatuses may be performed by more, fewer, or other components. For example, the operations of integrated circuit 128 and computing system 20 may be performed by one component, or the operations of image processor 44 may be performed by more than one component. Additionally, operations of the systems and apparatuses may be performed using any suitable logic comprising software, hardware, and/or other logic. As used in this document, "each" refers to each member of a set or each member of a subset of a set.

Modifications, additions, or omissions may be made to the methods disclosed herein without departing from the scope of the invention. The methods may include more, fewer, or other steps. Additionally, steps may be performed in any suitable order.

A component of the systems and apparatuses disclosed herein may include an interface, logic, memory, and/or other suitable element. An interface receives input, sends output, processes the input and/or output, and/or performs other suitable operation. An interface may comprise hardware and/or software.

Logic performs the operations of the component, for example, executes instructions to generate output from input. Logic may include hardware, software, and/or other logic. Logic may be encoded in one or more tangible media and may perform operations when executed by a computer. Certain logic, such as a processor, may manage the operation of a component. Examples of a processor include one or more computers, one or more microprocessors, one or more field programmable gate arrays, one or more digital signal processors, one or more applications, and/or other logic.

In particular embodiments, the operations of the embodiments may be performed by one or more computer readable media encoded with a computer program, software, computer executable instructions, and/or instructions capable of being executed by a computer. In particular embodiments, the operations of the embodiments may be performed by one or more field programmable gate arrays configured by firmware to implement logical functions. In particular embodiments, the operations of the embodiments may be performed by one or more computer readable media storing, embodied with, and/or encoded with a computer program and/or having a stored and/or an encoded computer program.

A memory stores information. A memory may comprise one or more non-transitory, tangible, computer-readable, and/or computer-executable storage media. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A method of producing infrared imagery comprising:
   for each of a plurality of frames, sampling a plurality of foveal array elements of a detector foveal region of a microbolometer array at a faster sampling rate to yield foveal array data;

sampling a plurality of peripheral array elements of a detector peripheral region of the microbolometer array at a slower sampling rate to yield peripheral array data, the plurality of peripheral array elements including a plurality of sub-regions, each sub-region including two or more peripheral array elements, and wherein sampling the plurality of peripheral array elements comprises for each sub-region:
sampling a first subset of the each sub-region for a first frame of the plurality of frames; and
sampling a second subset of the each sub-region for a second frame of the plurality of frames, the second subset not equal to the first subset;
processing the foveal array data to yield foveal image data for a display foveal region of a display; and
processing the peripheral array data to yield peripheral image data for a display peripheral region of the display.

2. The method of claim 1, wherein the first and second subsets are of each sub-region.

3. The method of claim 1, the processing the peripheral array data further comprising:
generating first image data generated from the first subset of the peripheral array elements for the first frame and the second frame; and
generating second image data generated from the second subset of the peripheral array elements for the second frame and a third frame.

4. The method of claim 1, the processing the peripheral array data further comprising:
generating first image data generated from the first subset of the peripheral array elements for the first frame; and
holding the first image data for the second frame.

5. The method of claim 1, the processing the peripheral array data further comprising:
generating first image data generated from the first subset of the peripheral array elements for the first frame; and
averaging the first image data with second image data generated from the second subset of the peripheral array elements for the second frame.

6. The method of claim 1, further comprising:
designating a plurality of array elements as the foveal array elements to set the foveal region.

7. The method of claim 1, further comprising setting the foveal region by:
sending one or more fovea start addresses and one or more fovea stop addresses to the microbolometer plane array.

8. The method of claim 1:
further comprising maintaining a constant bias duty cycle to compensate for an impact of one or more changes in Joule heating in one or more peripheral array elements as a sampling duty cycle changes.

9. The method of claim 1:
further comprising electronically adjusting one or more bias conditions of the microbolometer array to compensate for an impact of one or more changes in Joule heating in one or more peripheral array elements as a sampling duty cycle changes.

10. The method of claim 1:
further comprising electronically adjusting an operating bias of supporting circuitry of the microbolometer array to compensate for an impact of one or more changes in Joule heating in one or more peripheral array elements as a sampling duty cycle changes.

11. A system comprising:
a microbolometer array; and one or more processors operable to:
for each frame of a plurality of frames, sample a plurality of foveal array elements of a detector foveal region of the microbolometer array at a faster sampling rate to yield foveal array data;
sample a plurality of peripheral array elements of a detector peripheral region of the microbolometer array at a slower sampling rate to yield peripheral array data, wherein the plurality of peripheral array elements includes a plurality of sub-regions, each sub-region including two or more peripheral array elements, and sampling the peripheral array elements includes for each sub-region:
sampling a first subset of the each sub-region for a first frame; and
sampling a second subset of the each sub-region for a second frame, the second subset not equal to the first subset;
process the foveal array data to yield foveal image data for a display foveal region of a display; and
process the peripheral array data to yield peripheral image data for a display peripheral region of the display.

12. The system of claim 11, wherein the first and second subsets are
proper subsets of each sub-region.

13. The system of claim 11, the processing the peripheral array data further comprising:
generating first image data generated from the first subset of the peripheral array elements for the first frame and the second frame; and
generating second image data generated from the second subset of the peripheral array elements for the second frame and a third frame.

14. The system of claim 11, the processing the peripheral array data further comprising:
generating first image data generated from the first subset of the peripheral array elements for the first frame; and
holding the first image data for the second frame.

15. The system of claim 11, the processing the peripheral array data further comprising:
generating first image data generated from the first subset of the peripheral array elements for the first frame; and
averaging the first image data with second image data generated from the second subset of the peripheral array elements for the second frame.

16. The system of claim 11, the one or more processors further operable to set the foveal region by:
sending one or more fovea start addresses and one or more fovea stop addresses to the microbolometer array.

17. The system of claim 11:
the one or more processors further operable to maintain a constant bias duty cycle to compensate for an impact of one or more changes in Joule heating in one or more peripheral array elements as a sampling duty cycle changes.

18. The system of claim 11:
the one or more processors further operable to electronically adjust one or more bias conditions of the microbolometer array to compensate for an impact of one or more changes in Joule heating in one or more peripheral array elements as a sampling duty cycle changes.

* * * * *

UNITED STATES PATENT AND TRADEMARK OFFICE
CERTIFICATE OF CORRECTION

PATENT NO.        : 8,511,823 B2
APPLICATION NO.   : 13/026854
DATED             : August 20, 2013
INVENTOR(S)       : Stephen H. Black et al.

It is certified that error appears in the above-identified patent and that said Letters Patent is hereby corrected as shown below:

In the Claims:

In claim 2, column 7, line 20, "subsets are of each sub-region" should be
--subsets are proper subsets of each sub-region--.

Signed and Sealed this
Tenth Day of December, 2013

Margaret A. Focarino
*Commissioner for Patents of the United States Patent and Trademark Office*